United States Patent [19]

Broze, Jr. et al.

[11] Patent Number: 5,106,833
[45] Date of Patent: Apr. 21, 1992

[54] COAGULATION INHIBITORS

[75] Inventors: George J. Broze, Jr.; Thomas J. Girard, both of St. Louis, Mo.

[73] Assignee: Washington University, St. Louis, Mo.

[21] Appl. No.: 301,779

[22] Filed: Jan. 26, 1989

Related U.S. Application Data

[63] Continuation-in-part of Ser. No. 77,366, Jul. 23, 1987, and Ser. No. 123,753, Nov. 23, 1987, Pat. No. 4,966,852.

[51] Int. Cl.[5] .................. A61K 37/02; C07K 3/00
[52] U.S. Cl. .................... 514/12; 424/529; 530/300; 530/350
[58] Field of Search ............. 424/101, 529; 530/380, 530/381, 384, 300, 350; 514/12

[56] References Cited

U.S. PATENT DOCUMENTS 4,966,852 10/1990 Wun et al. ............................ 435/235

OTHER PUBLICATIONS

Day et al., Blood, vol. 76, No. 8 (Oct. 1990), 1538-45.
Girard et al., Nature, vol. 338 (Apr. 1989) 518.
Broze & Miletich, Proc. Nat'l. Acad. Sci. U.S.A. 84, 1886-1890 (1987).
Wun et al., J. Biol. Chem. 263 (13), 6001-6014 (1988).
Broze et al., Blood 71 (2), 335-343 (1988).
Broze et al., Thromb. Res. 48, 253-259 (1987).
Novotny et al., Blood 72 (6), 2020-2025 (1988).
Gebward et al., (1986), "Protease Inhibitors", (Barret & Salvesen eds.) 375-383 as cited in Broze et al. Biochem. vol. 29, No. 33, Aug. 1990, 7539.
Hochstrasser et al., CA 91(25):206327Z (1979).
Sanders et al., Blood, vol. 66, No. 1 (Jul. 1985) 204.
Wachter et al., CA 91 (25): 206328a (1979).
Rudinger, "Peptide Hormones", (ed. JA Parsons 1976) 1-6.

Primary Examiner—Lester L. Lee
Assistant Examiner—B. Celsa
Attorney, Agent, or Firm—Scott J. Meyer; James W. Williams, Jr.

[57] ABSTRACT

Novel blood coagulation inhibitors are disclosed which are peptide fragments comprising (A) Kunitz-type domain two of lipoprotein-associated coagulation inhibitor which inhibits Factor Xa production and (B) Kunitz-type domains one and two of lipoprotein-associated coagulation inhibitor which inhibits Factor VIIa/TF enzymatic complex formation.

3 Claims, 5 Drawing Sheets

COAGULATION INHIBITORS

CROSS-REFERENCE TO RELATED APPLICATIONS

This is a continuation-in-part of copending application Ser. No. 07/77,366, filed July 23, 1987 and application Ser. No. 07/123,753, filed Nov. 23, 1987 now U.S. Pat. No. 4,966,852.

BACKGROUND OF THE INVENTION

This invention relates to novel peptide fragments of a blood coagulation inhibitor known as tissue factor inhibitor (TFI) but preferably as lipoprotein-associated coagulation inhibitor (LACI). More particularly, the invention relates to a method of inhibiting Factor Xa or Factor VIIa/TF complex with novel peptide fragments of LACI.

The coagulation cascade that occurs in mammalian blood comprises two distinct systems—the so-called intrinsic and extrinsic systems. The latter system is activated by exposure of blood to tissue thromboplastin (Factor III), hereinafter referred to as tissue factor (TF). Tissue factor is a lipoprotein that arises in the plasma membrane of many cell types and in which the brain and lung are particularly rich. Upon coming into contact with TF, plasma Factor VII or its activated form, Factor VII$_a$, forms a calcium-dependent complex with TF and then proteolytically activates Factor X to Factor X$_a$, and Factor IX to Factor IX$_a$, thereby triggering a cascade of events which leads eventually to the formation of thrombin and a fibrin clot.

In copending application Ser. No. 07/77,366, filed July 23, 1987, a purified tissue factor inhibitor (TFI) is disclosed which was secreted from HepG2 cells. It was found to exist in two forms, a TFI$_1$, migrating at about 37–40,000 daltons and a TFI$_2$ at about 25–26,000 daltons, as determined by sodium dodecylsulfate polyacrylamide gel electrophoresis (SDS-PAGE). A partial N-terminal amino acid sequence for the TFI was assigned as:

```
1                                                           15
X—X—Glu—Glu—Asp—Glu—Glu—His—Thr—Ile—Ile—Thr—Asp—Thr—Glu—

16                                          27
Leu—Pro—Pro—Leu—Lys—Leu—Met—His—Ser—Phe—(Phe)—Ala
``` wherein X—X had not been determined. The disclosure of said application and the related disclosure by Broze and Miletich, *Proc. Natl. Acad. Sci. USA* 84, 1886–1990 (1987) are incorporated herein by reference.

In copending application Ser. No. 07/123,753, filed Nov. 23, 1987, the complete coding sequence of a cDNA clone representing essentially the full size TFI or LACI is disclosed. The cDNA sequence encoded a 31,950 Dalton protein of 276 amino acids which included 18 cysteines and 7 methionines. The translated amino acid sequence showed that a signal peptide of about 28 amino acids preceded the mature LACI protein. The "mature" LACI was defined to include both LACI and methionyl LACI by virtue of the ATG translational codon in the λP9 clone described therein.

There are three potential N-linked glycosylation sites in the LACI protein with the sequence Asn-X-Ser/Thr, wherein X can be any of the common 20 amino acids. These sites are at amino acid positions Asn 145, Asn 195, and Asn 256, when the first methionine after the 5'-noncoding region is assigned amino acid position +1.

The translated amino acid sequence of LACI showed several discernible domains, including a highly negatively charged N-terminal, a highly positively charged carboxy-terminal, and an intervening portion consisting of 3 homologous domains with sequences typical of Kunitz-type enzyme inhibitors. Based on a homology study, LACI appeared to be a member of the basic protease inhibitor gene superfamily.

In said copending application Ser. No. 07/123,753, the three tandemly repeated Kunitz-type serine protease inhibitory domains were shown to exist at LACI amino acid residues 47–117 (1), 118–188 (2) and 210–280 (3), respectively, based on the above amino acid numbering system. The disclosure of said application and the related disclosure by Wun et al., *J. Biol. Chem.* 263 (13), 6001–6004 (1988) are incorporated herein by reference.

BRIEF DESCRIPTION OF THE INVENTION

In accordance with the present invention, novel peptide fragments of lipoprotein-associated coagulation inhibitor (LACI) are provided for inhibiting Factor Xa or Factor VIIa/TF complex. It has been found, surprisingly, that whereas both Kunitz-type domains one and two of LACI are required for inhibition of Factor VIIa/TF complex activity, only the second of these domains is required for efficient binding and inhibition of Factor Xa. The third domain appears to be unnecessary for these inhibitory activities.

Using the previous numbering system in which amino acid +1 was assigned to the first methionine after a stop codon in the 5'-noncoding region, the three Kunitz-type domains were described as LACI(47–117), LACI(118–188) and LACI(210–280), respectively. In a preferred numbering system used hereinafter in which amino acid +1 is assigned to the NH$_2$-terminus of the 276 amino acid protein, the corresponding Kunitz-type domains can be designated LACI(19–89), LACI(90–160) and LACI(182–252), respectively. So also, the peptide fragment comprising Kunitz-type domains one and two can be designated LACI(19–160). It will be appreciated, however, that variations in length and composition of these domains or the individual internal amino acids which do not adversely or detrimentally affect the biological activity of the domains as defined herein are included within the scope of the invention. Thus, the Kunitz-type domains one and two of LACI which are required for inhibition of Factor VIIa/TF complex activity can be extended to also include the first 18 amino acid residues of the NH$_2$-terminus of LACI. This peptide fragment can be designated LACI(-1–160).

DETAILED DESCRIPTION OF THE INVENTION

Figure 1:
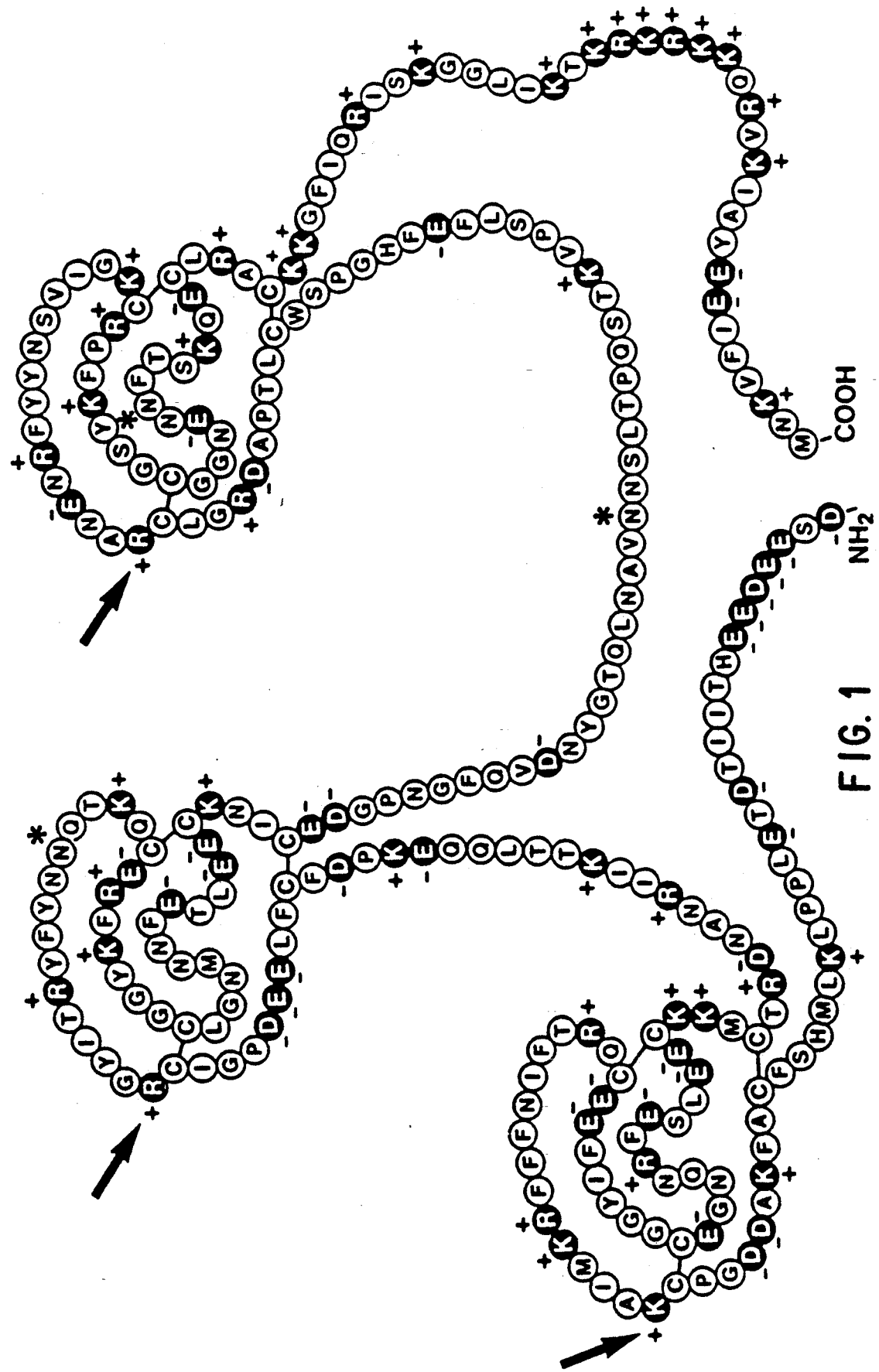

While the specification concludes with claims particularly pointing out and distinctly claiming the subject matter regarded as forming the present invention, it is believed that the invention will be better understood from the following detailed description of preferred embodiments of the invention taken in conjunction with the appended drawings, in which:

FIG. 1 is a schematic diagram of LACI's predicted secondary structure showing the sulfhydryl bonding for the three Kunitz domains. The Kunitz domains are referred to by number as they occur from the $NH_2$-terminus. The arrows indicate the location of the presumed P1 residues of the active site clefts for the Kunitz domains. The charges for the amino acid side chains are indicated (histidine side chains were considered to be uncharged). Asterisks demarcate the potential sites for N-linked glycosylation.

Figure 2:
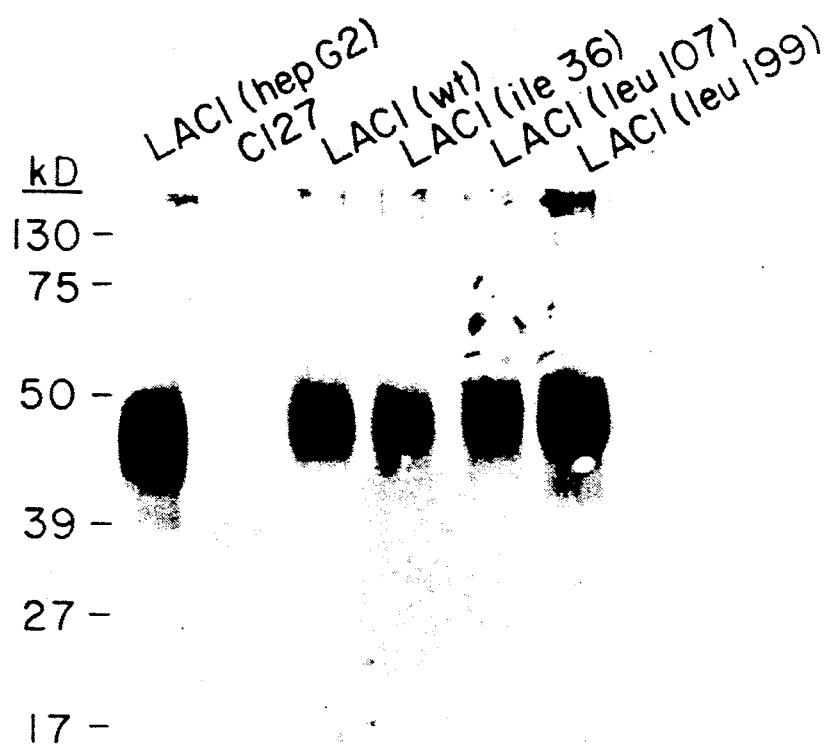

FIG. 2 is a Western blot showing the expression of the recombinant wild-type and mutant LACIs. Serum-free conditioned media (100 μl) from the indicated cells and 20 ng of purified LACI(HepG2) were run in a 15% polyacrylamide gel, transferred to nitrocellulose, probed with mouse polyclonal anti-LACI antibodies and colorimetrically developed.

Figure 3:
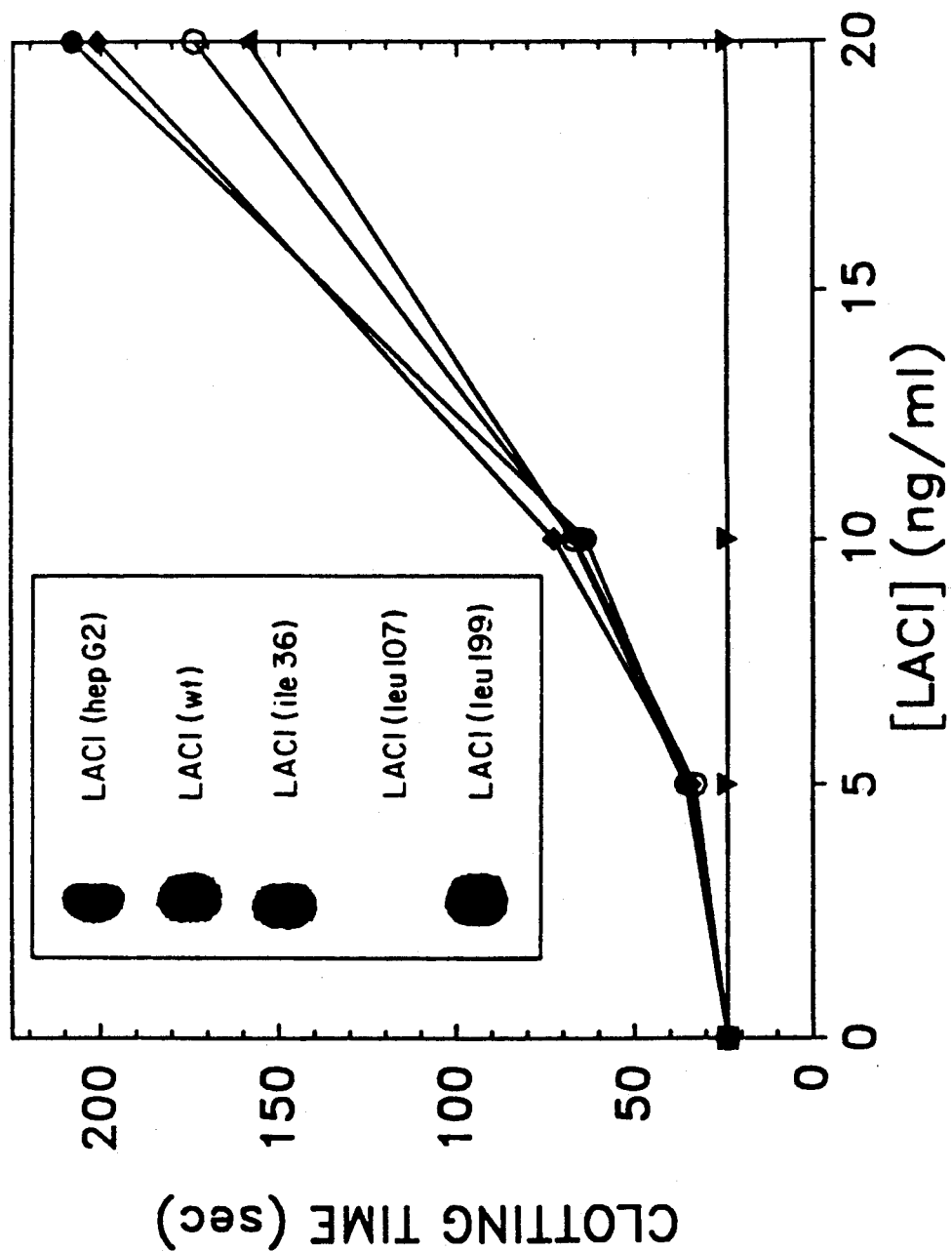

FIG. 3 is a graphical representation which shows the binding and inhibition of Factor Xa by wild-type and mutant LACIs. Factor $X_a$ inhibitory activities were determined as previously described by Broze et al., *Blood* 71, 335-343 (1988), using 25 ng/ml bovine Factor Xa (final concentration). Samples are: LACI(HepG2) (o); LACI(wt) (•); LACI(Ile-36) (▲); LACI(Leu-107) (▼); LACI(Leu-199) (♦) Inset, $^{125}$I-Xa blot analysis of LACI mutants. Samples are designated by the mutation as in FIG. 2.

Figure 4A:
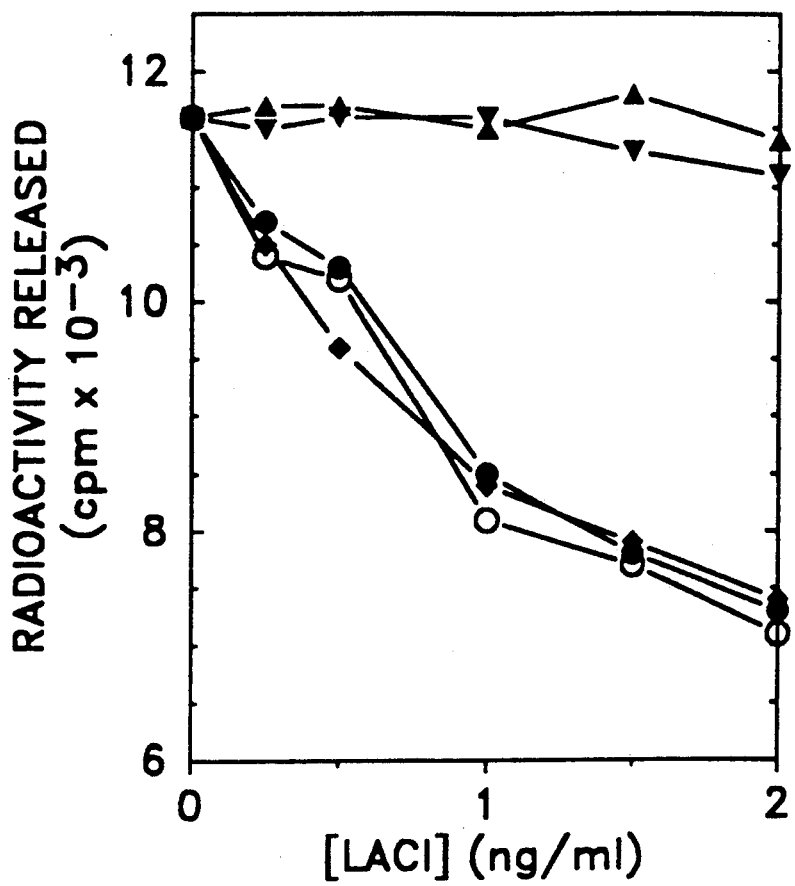
Figure 4B:
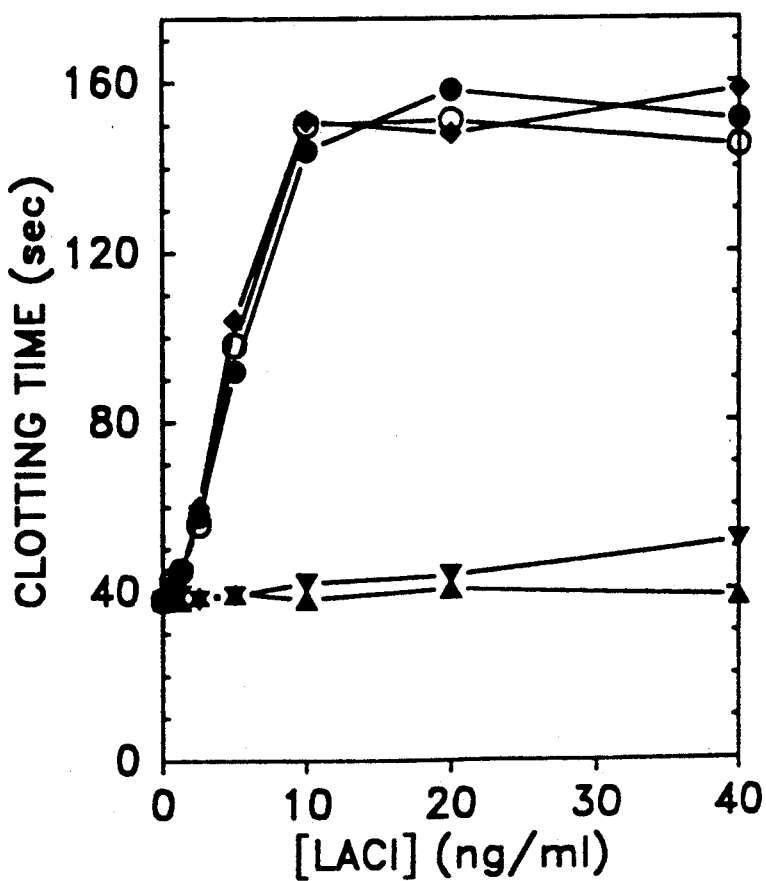

FIGS. 4a and 4b are a graphical representation which shows VII(a)/TF inhibitory activities of the wild-type and mutant LACIs in panel 4(a), as measured in a $^3$H-IX activation peptide release assay, and in panel 4(b), as measured in a three stage clotting assay. Both assays were performed as previously described by Broze et al., *Blood* 71, 335-343 (1988), with LACI(HepG2) (o); LACI(wt) (•); LACI(Ile-36) (▲); LACI(Leu-107) (▼) LACI(Leu-199) (♦).

Figure 5:
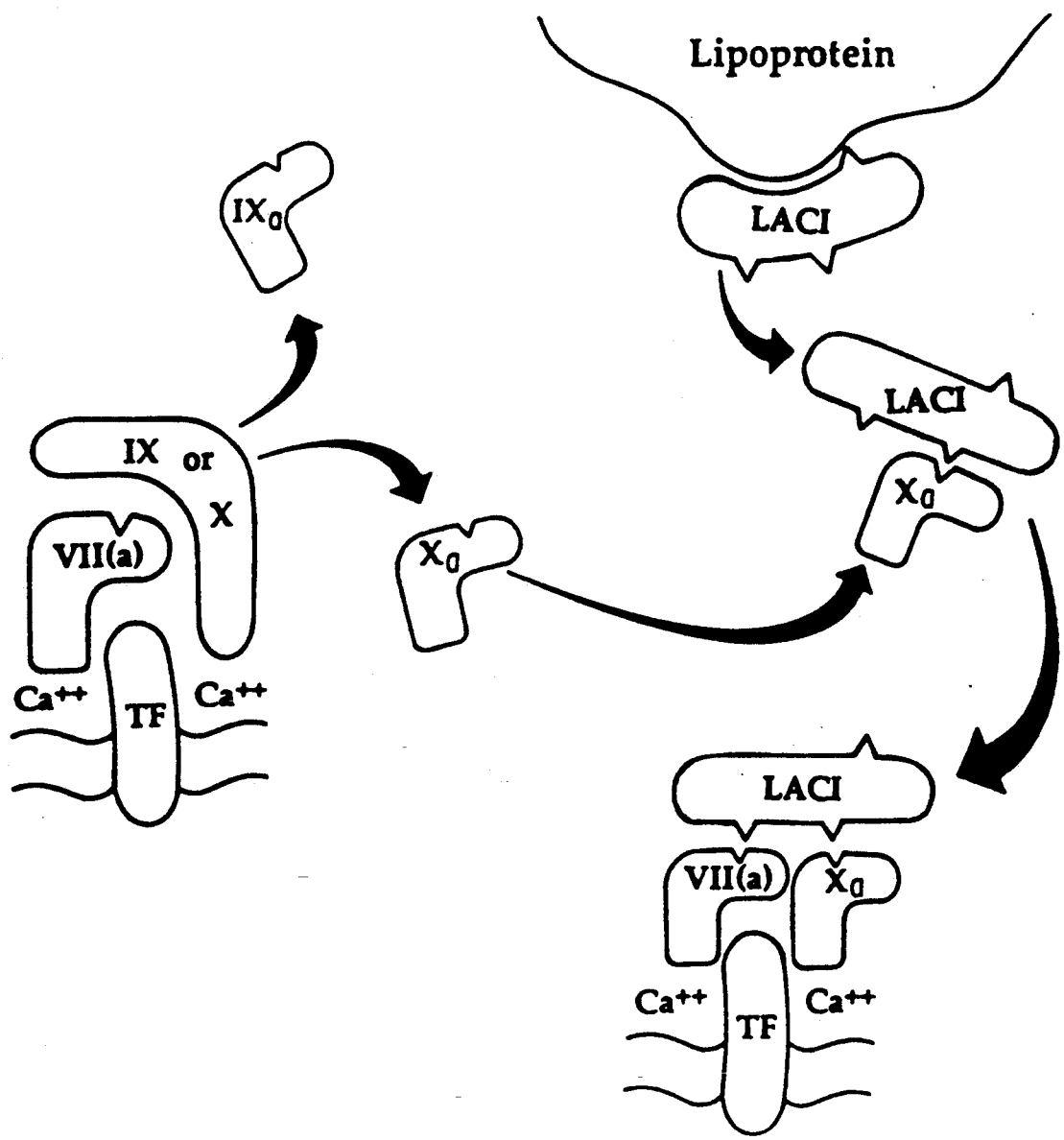

FIG. 5 is a schematic of the proposed mechanism for the inhibition of Factor Xa and the VII/TF complex by LACI. VII(a) connotes either VII or VIIa; the indentations represent the active sites for VII/VIIa and Xa; and the protrusions represent LACIs' three Kunitz domains. In the Xa/LACI complex, the active site of Xa is bound to the second Kunitz domain of LACI. In the final quarternary Xa/LACI/VII(a)/TF complex, Xa is bound at its active site to LACI's second Kunitz domain and VII(a) is bound at its active site to the first Kunitz domain of LACI. The mechanism of the association of LACI with lipoproteins is not presently known.

The following exemplary laboratory preparative work was carried out to generate the results shown in the foregoing figures:

EXAMPLE 1

A modified LACI cDNA insert engineered into a bovine papilloma virus vector for expression in C127 fibroblasts was ligated into vector M13mp18 and site-directed mutagenesis [Zoller and Smith, *Meth. Enzymol.* 100, 468-500 (1983)] was performed as follows: LACI-(Ile-36) A→T at bp 572 which changes Lys-36 to Ile; LACI(Leu-107) G→T at bp 785 which changes Arg-107 to Leu; and LACI(Leu-199) G→T at bp 1061 which changes Arg-199 to Leu. LACI(wt) is recombinant wild-type LACI. Sequences of the mutant molecules were confirmed by the dideoxy chain termination procedure of Sanger et al., *Proc. Natl. Acad. Sci. USA* 83, 6776-6780 (1977), and cloned into the bovine papilloma virus expression vector pMON1123. Each of these expression vectors plus pSV2neo were cotransfected into mouse C127 fibroblasts using the calcium phosphate precipitation procedure of Howley et al., *Meth. Enzymol.* 101, 387-403 (1983), and G418 resistant clones were screened for expression of LACI. LACI(HepG2) was purified as previously described by Broze et al., *Thromb. Res.* 48, 253-259 (1987). The numbering of the nucleotides is based on a 4.0 kb LACI cDNA sequence.

EXAMPLE 2

LACIs were precipitated from transfected cell clones' serum-free conditioned media using $CdCl_2$, resuspended in 0.25 M EDTA, pH 9.0, clarified and dialyzed into 0.1 M NaCl, 0.05 M tris-HCl, pH 7.5 (TS) [Broze et al., *Thromb. Res.* 48, 253-259 (1987)]. Recombinant LACIs were purified using a mouse monoclonal anti-LACI-Affigel 10 column. Dialyzed $CdCl_2$ concentrated LACI samples were applied to the column in TS, the column was washed with several volumes of TS and LACI subsequently eluted with 2 M NaSCN. Following the addition of bovine serum albumin as carrier, concentration and dialyses into TS, the LACI concentration for each sample was determined in a particle-concentration immunofluoresence assay [Miletich et al., *N. Eng. J Med.* 317, 991-996 (1987)] using two non-competitive anti-LACI monoclonal antibodies. For the ligand blot, 50 ng of each sample was electrophoretically fractionated by SDS-PAGE, transferred to nitrocellulose, and then probed with $^{125}$I-Xa [Novotny et al., *Blood* 72, 2020-2025 (1988)]. Western analysis using rabbit polyclonal anti-LACI antibodies was performed on a duplicate blot to confirm that equivalent amounts of LACI were present in each sample (data not shown).

In thus demonstrating the invention and the useful relationships of the Kunitz structures to LACI's function in the above examples, site-directed mutagenesis was employed to produce altered forms of LACI in which the residue at the active site cleft of each Kunitz domain has been individually changed. Functional assays using the altered LACIs indicated that the second Kunitz domain is required for efficient binding and inhibition of Xa and that both Kunitz domains one and two are required for the inhibition of VIIa/TF activity. Alteration of the active site residue of the third Kunitz domain had no significant effect on either Xa binding or VIIa/TF inhibition. It is concluded that in the putative Xa/LACI/VIIa/TF inhibitory complex, LACI's first Kunitz domain is bound to the active site of VIIa/TF and that the second Kunitz domain is bound to Xa's active site.

By sequence homology alignment with bovine pancreatic trypsin inhibitor (BPTI, aprotinin), the P1 position for each of LACI's Kunitz domains was identified (FIG. 1). Site-directed mutagenesis was used to prepare LACI mutants in which this active site cleft residue in each Kunitz domain has been individually changed. These mutated LACI DNAs were introduced into the bovine papilloma virus vector pMON1123 and cotransfected with pSV2neo into mouse C127 fibroblasts. pMON1123 contains the entire bovine papilloma virus genome ligated to the pBR322 derivative of pML2. The inserts were ligated into the vector's unique BamHI site located between a mouse metallothionein I promoter and SV40 late polyadenylation sequence. Individual clones expressing human LACI messages (data not shown) and LACI protein were identified (FIG. 2) and recombinant LACIs were isolated from the clones' conditioned media using monoclonal anti-LACI affinity chromatography.

LACI isolated from the conditioned media of a human hepatoma cell line (HepG2) as well as that isolated from plasma bind $^{125}$I-labeled factor Xa on ligand blots and inhibit factor Xa enzymatic activity [Broze et al., *Blood* 71, 335-343 (1988); Novotny et al., *Ibid.* 72, 2020-2025 (1988)]. The ability of the mutant LACI molecules to bind to and inhibit factor Xa was analyzed. LACI(Ile-36) and LACI(Leu-199) with an altered active site residue for Kunitz domains one and three, respectively, both bound $^{125}$-Xa on ligand blots and inhibited factor Xa to a similar degree as LACI(wt) or LACI(HepG2). LACI(Leu-107), which contains an altered active site residue in the second Kunitz domain, however, was not recognized by $^{125}$I-Xa, nor did it inhibit factor Xa functional activity (FIG. 3). These results indicate that the second Kunitz domain is responsible for LACI's factor Xa binding and inhibitory activity.

The ability of the altered LACIs to inhibit VII(a)/TF activity in the presence of Xa was determined using two separate assays. In the first, VII(a)/TF activity was determined by the releases of the activation peptide from its substrate factor IX. As the results in FIG. 4A show, LACI(Leu-199), which contains an altered third Kunitz domain, inhibited the VII(a)/TF activity to a similar degree as LACI(wt) and LACI(HepG2). However, mutation of either the first Kunitz domain, LACI-(Ile-36), or the second Kunitz domain, LACI(Leu-107), resulted in the loss of VII(a)/TF inhibitory activity.

Similar results were obtained for the mutants in a three stage clotting assay which is dependent on VII-(a)/TF activation of its other substrate, factor X. In this assay, inhibition of VII(a)/TF activity causes less factor X to be activated in the second stage resulting in the prolongation of the clotting time. Again, mutation of the active site residue in either the first or second Kunitz domain abrogated LACI's ability to effectively inhibit VII(a)/TF activity, whereas mutation of the third Kunitz domain had no effect on activity. At high concentrations of LACI(Leu-107) a slight, reproducible inhibition was observed (FIG. 4B). Like the other functioning LACIs, this low level of inhibition was dependent on the presence of saturating amounts of factor X (which is converted to Xa) in the first stage of the assay (data not shown).

From these results it is concluded that LACI's first two Kunitz domains are necessary for the inhibition of VII(a)/TF activity and that the second Kunitz domain is responsible for factor Xa binding and inhibition. Alteration of the active site cleft residue for the third Kunitz domain did not effect either Xa or VII(a)/TF inhibitory activity, thereby suggesting that it is not required for these functional properties of LACI. It is conceivable that changing Arg-199 to Leu in this domain was not sufficient to effect the functional activity of the third domain (whatever it may be) but this is believed to be unlikely.

Although the inventor is not bound by theory, a working hypothesis for the mechanism by which LACI inhibits VII(a)/TF activity is schematically shown in FIG. 5. When plasma is exposed to TF, VII(a) binds to TF and activates factors IX and X. Some of the Xa generated becomes bound to LACI's second Kunitz domain and is inhibited. The Xa/LACI complex then binds to and inhibits the VII(a)/TF complex presumably by forming a Xa/LACI/VII(a)/TF quarternary complex. It has been previously shown that the NH$_2$-terminal domain of Xa, containing its $\gamma$-carboxyglutamic acids which are required for Ca$^{++}$ binding, is necessary for inhibition of VII(a)/TF activity by the LACI/Xa complex. See Broze et al., *Blood* 71, 335-343, (1988). Results presented here indicate that in addition to the second Kunitz domain, which is necessary for the formation of the Xa/LACI complex, LACI's first Kunitz domain is also required for VII(a)/TF inhibition, presumably mediated through its binding to the active site of VII(a). The third Kunitz domain of LACI, however, does not appear to be required for these functions.

Various other examples will be apparent to the person skilled in the art after reading the present disclosure without departing from the spirit and scope of the invention. It is intended that all such further examples be included within the scope of the appended claims.

What is claimed is:

1. A novel blood coagulation inhibitor selected from the group consisting of
   (A) a peptide fragment of lipoprotein-associated coagulation inhibitor having the sequence of residues 90 to 160 of the 276 residue mature LACI protein, and
   (B) a peptide fragment of lipoprotein-associated coagulation inhibitor having the sequence of residues 19 to 160 or 1 to 160 of the 276 residue mature LACI protein.

2. A method of inhibiting Factor Xa production in a mammal comprising administering to said mammal an effective amount of a peptide fragment of lipoprotein-associated coagulation inhibitor having the sequence of residues 90 to 160 of the 276 residue mature LACI protein.

3. A method of inhibiting Factor VIIa/TF enzymatic complex formation in a mammal comprising administering to said mammal an effective amount of a peptide fragment of lipoprotein-associated coagulation inhibitor having the sequence of residues 19 to 160 or 1 to 160 of the 276 residue mature LACI protein.

* * * * *